United States Patent
Mathew et al.

(10) Patent No.: US 10,231,667 B2
(45) Date of Patent: Mar. 19, 2019

(54) NON-INVASIVE DEHYDRATION MONITORING

(71) Applicant: KONINKLIJKE PHILIPS N.V., Eindhoven (NL)

(72) Inventors: Denny Mathew, Eindhoven (NL); Kiran Hamilton J. Dellimore, Eindhoven (NL); Rick Bezemer, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 439 days.

(21) Appl. No.: 14/923,007

(22) Filed: Oct. 26, 2015

(65) Prior Publication Data
US 2016/0120468 A1 May 5, 2016

(30) Foreign Application Priority Data
Oct. 31, 2014 (EP) .................................. 14191241

(51) Int. Cl.
*A61B 5/00* (2006.01)
*A61B 5/024* (2006.01)
(Continued)

(52) U.S. Cl.
CPC .......... *A61B 5/4875* (2013.01); *A61B 5/0059* (2013.01); *A61B 5/0088* (2013.01);
(Continued)

(58) Field of Classification Search
CPC ....... A61B 5/0059; A61B 5/4875; A61B 5/01; A61B 5/0088; A61B 5/0537; A61B 5/0205; A61B 5/02416; A61B 5/0531
See application file for complete search history.

(56) References Cited

U.S. PATENT DOCUMENTS

| 4,398,541 A | 8/1983 | Pugliese |
| 4,718,417 A * | 1/1988 | Kittrell .............. A61B 1/00183 600/317 |

(Continued)

FOREIGN PATENT DOCUMENTS

| EP | 1543768 A1 | 6/2005 |
| EP | 2387942 A1 | 11/2011 |

(Continued)

OTHER PUBLICATIONS

Verkruysse, Wim et al "Remote Plethysmographic Imaging using Ambient Light" Optics Express, vol. 16, No. 26, Dec. 2008.

(Continued)

*Primary Examiner* — Nathan J Jenness

(57) ABSTRACT

The present invention relates to a device (10) and method for non-invasively measuring a hydration state of a living being (62). To improve with respect to the convenience-to-use, the cost-effectiveness and the accuracy of the delivered results, the proposed device comprises a first light source (14) for emitting light of a first wavelength into a tissue portion (12) of the living being (62), polarization means (18) for polarizing at least part of the emitted light prior to an interaction of the emitted light with the tissue portion (12), a first light detector (26) for detecting polarized light of the first wavelength reflected at the tissue portion (12) and processing means (32) configured to derive a tissue hydration parameter from the detected reflected polarized light and to determine a body hydration index based on said tissue hydration parameter.

22 Claims, 5 Drawing Sheets

(51) Int. Cl.
*A61B 5/0205* (2006.01)
*A61B 5/01* (2006.01)
*A61B 5/08* (2006.01)
*A61B 5/053* (2006.01)
*A61B 5/087* (2006.01)
*A61B 5/1455* (2006.01)

(52) U.S. Cl.
CPC .............. *A61B 5/01* (2013.01); *A61B 5/0205* (2013.01); *A61B 5/0537* (2013.01); *A61B 5/082* (2013.01); *A61B 5/486* (2013.01); *A61B 5/682* (2013.01); *A61B 5/7278* (2013.01); *A61B 5/02416* (2013.01); *A61B 5/0531* (2013.01); *A61B 5/087* (2013.01); *A61B 5/14551* (2013.01); *A61B 2562/0238* (2013.01)

(56) References Cited

U.S. PATENT DOCUMENTS

| | | | |
|---|---|---|---|
| 5,205,281 A | 4/1993 | Buchanan | |
| 7,319,894 B2 | 1/2008 | Higgins | |
| 7,515,952 B2 | 4/2009 | Balas | |
| 8,352,005 B2 | 1/2013 | Esenaliev | |
| 2005/0185847 A1* | 8/2005 | Rowe | G06K 9/00006 382/224 |
| 2006/0239547 A1 | 10/2006 | Robinson | |
| 2007/0048224 A1 | 3/2007 | Howell | |
| 2008/0012582 A1 | 1/2008 | Jang | |
| 2008/0281170 A1* | 11/2008 | Eshelman | A61B 5/0205 600/301 |
| 2009/0043179 A1 | 2/2009 | Melker | |
| 2010/0185064 A1* | 7/2010 | Bandic | A61B 5/0059 600/306 |
| 2010/0245823 A1* | 9/2010 | Chhibber | A61B 5/0059 356/366 |
| 2011/0288385 A1* | 11/2011 | Stamatas | A61B 5/0059 600/306 |
| 2012/0083711 A1 | 4/2012 | Goldstein | |
| 2013/0144136 A1* | 6/2013 | Rymut | A61B 5/0059 600/310 |
| 2014/0107443 A1 | 4/2014 | Hoarau | |
| 2014/0171759 A1 | 6/2014 | White | |
| 2014/0323829 A1 | 10/2014 | Leboeuf | |
| 2015/0088431 A1* | 3/2015 | Podhajsky | A61B 5/0059 702/19 |
| 2015/0351699 A1* | 12/2015 | Addison | A61B 5/7221 600/301 |

FOREIGN PATENT DOCUMENTS

| | | |
|---|---|---|
| WO | 2004028359 A1 | 4/2004 |
| WO | 2009027898 A1 | 3/2009 |
| WO | 2009053920 A1 | 4/2009 |
| WO | 2010111463 A1 | 9/2010 |
| WO | 2013027141 A2 | 2/2013 |
| WO | 2014041584 A1 | 3/2014 |

OTHER PUBLICATIONS

Yess, Sinclair et al "A Proposed Miniature Red/Infrared Oximeter Suitable for Mounting on a Catheter Tip", IEEE Tans. Biomedical Eng. 1977.

* cited by examiner

| DEHYDRATION | 0 | 1 | 2 | 3 |
|---|---|---|---|---|
| *Tissue reflectivity [%]* | 'normal' | +10% | +20% | +30% |
| *Tissue color [mV]* | 'normal' | +10% | +20% | +30% |
| Body temperature [°C] | ≤38 | 38-39 | 39-40 | >40 |
| Heart rate [bpm] | ≤80 | 80-90 | 90-100 | >100 |
| Breathing rate [bpm] | 9-14 | 15-20 | 21-29 | >30 |

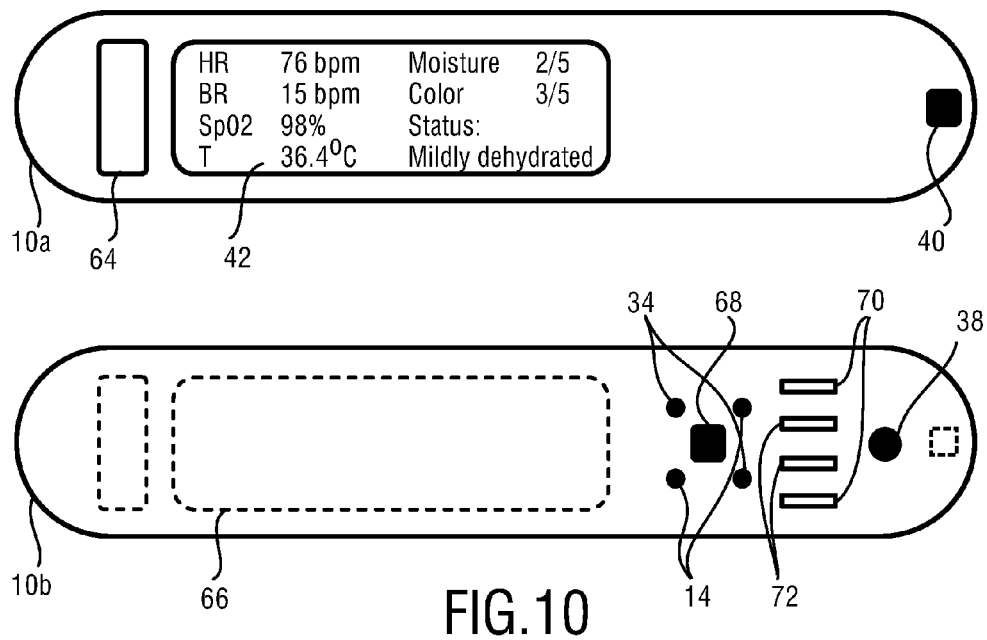
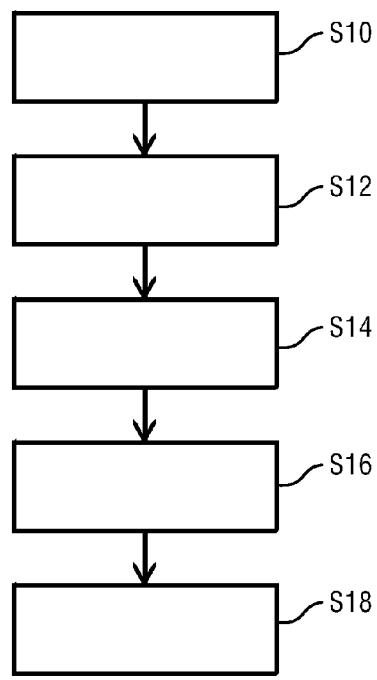
FIG.10
FIG.11

NON-INVASIVE DEHYDRATION MONITORING

CROSS-REFERENCE TO PRIOR APPLICATIONS

This application claims the benefit of European Patent Application No. 14191241.0, filed on Oct. 31, 2014 which is hereby incorporated by reference herein.

FIELD OF THE INVENTION

The present invention relates to a device for measuring a hydration state of a living being as well as to a corresponding method.

BACKGROUND OF THE INVENTION

Dehydration, particularly from gastroenteritis or other illnesses that causes vomiting, diarrhea and fever (e.g. pyloric stenosis, thyrotoxicosis, diabetes insipidus, cystic fibrosis, bowel ischemia, etc.), is a common pediatric complaint. According to the Centers for Disease Control and Prevention, for children younger than 5 years, the annual incidence of diarrheal illness is approximately 1.5 billion, while deaths are estimated at between 1.5 and 2.5 million per year. Furthermore, there is substantial evidence to show that aging causes changes in body water composition, and that renal function and thirst perception on average decline among older adults. These three factors account for the prevalence of dehydration among the older adult population. In a study, dehydration was diagnosed in 6.7% of hospitalized patients aged 65 and over. Furthermore, 1.4% of the patients had dehydration as the principal diagnosis. Prospective studies in long-term care facilities (LTCs) showed that residents were dehydrated in 50% of the febrile episodes and that 27% of the LTC resident population referred to hospitals was admitted due to dehydration.

Dehydration is not only a common but also a very serious condition in older adults. The mortality of elderly patients with dehydration is high if not treated adequately and in some studies exceeds 50%. In terms of morbidity, several studies showed an association between high degrees of dehydration and poor mental function. Further, it was found that dehydration was a significant risk factor for developing thrombo-embolic complications, infectious diseases, kidney stones, and obstipation.

Although dehydration is almost always avoidable it is often not identified quickly enough in the hospital or primary care environment. While individuals who are able to manage their own fluid intake are also considered to be at risk, the elderly and young children are often most vulnerable. For the elderly this is often due to reduced renal function, decreased thirst sensation and increased susceptibility to long-term conditions such as diabetes. For pediatric populations this is because infants and children are very susceptible to volume depletion since they have higher body water content relative to adults, along with higher metabolic rates and increased body surface area to mass index, which means that they require proportionally greater volumes of water than adults in order to maintain their fluid equilibrium.

The clinical assessment of dehydration is difficult and highly subjective. Common features of dehydration are dry mouth, dry and dark colored tongue, increased pulse rate, weak pulse pressure and strength, increased breathing rate, elevated body temperature (i.e. fever), lateral furrowing and cracking of the tongue, and indentation of the teeth on the gums. In addition, in infants and young children other subjective signs including eye appearance, fontanel (soft spot) appearance, activity level and skin turgor are also routinely used in the diagnosis of dehydration.

As a result of the difficulty in reliably assessing the range of clinically relevant physiological signs of dehydration owing to the high degree of subjectivity required, there is a significant need for an objective measure of the hydration status of an individual, especially from elderly and pediatric population groups, which is reliable, easy to use and clinically relevant.

Testing or monitoring of dehydration status in very young and old patients is a difficult and complex issue for health workers. When not diagnosed in time, dehydration can have a profound effect on the health of patients in the form of malnutrition, renal failure, liver failure, deep vein thrombosis. Sometimes these effects can be fatal. Total body water and serum osmolality measurements are the well accepted techniques for measuring dehydration levels, but are both invasive and time consuming.

In US 2007/0048224 A1 a hydration sensor or sensing element configured to measure the hydration level of a user is disclosed. The sensing element can include a water-permeable material positioned in between two water-impermeable materials. The sensing element can be coupled to a bottle of fluid, or a carrier with a timer. The sensing element can be incorporated into a handheld device. The sensing element can be a disposable element, an element applicable for more than one-time use, or a re-usable element. The sensing element or sensor can be calibrated for a specific user or a group of users. One or more additional sensors that do not measure hydration level of the user can be coupled to a hydration sensing element to determine the amount of fluid consumption for the user in different conditions.

In WO 2009/027898 A1 a method and apparatses for measuring skin properties are disclosed. To improve the accuracy of detection of the dehydration level, an apparatus is presented that comprises: a positioning unit configured to position the apparatus over the piece of skin; a laser sensor configured to measure the distance between the laser sensor and the piece of skin by utilizing the self-mixing technology; wherein the positioning unit is further configured to generate a negative pressure on the piece of skin so as to raise the surface of the piece of skin, and position the laser sensor at a pre-determined location.

However, there is still a need for practical, user-friendly and reliable detection and early warning of dehydration.

SUMMARY OF THE INVENTION

It is an object of the present invention to provide a device for non-invasively measuring a hydration state of a living being as well as a corresponding method. In particular, improvements with respect to the convenience-to-use, the cost-effectiveness and the accuracy of the delivered results are needed.

In a first aspect of the present invention a device for measuring a hydration state of a living being is presented. The device comprises:

a first light source for emitting light of a first wavelength into a tissue portion of the living being;

polarization means for polarizing at least part of the emitted light prior to an interaction of the emitted light with the tissue portion;

a first light detector for detecting polarized light of the first wavelength reflected at the tissue portion, which has retained its polarization in the reflection; and processing means configured to derive a tissue hydration parameter from an intensity of the detected reflected polarized light and to determine a body hydration index based on said tissue hydration parameter.

In another aspect of the present invention a method for measuring a hydration state of a living being is presented. The method comprises the steps of:

emitting light of a first wavelength into a tissue portion of the living being;

polarizing at least part of the emitted light prior to an interaction of the emitted light with the tissue portion;

detecting polarized light of the first wavelength reflected at the tissue portion, which has retained its polarization in the reflection; and deriving a tissue hydration parameter from an intensity of the detected reflected polarized light and determining a body hydration index based on said tissue hydration parameter.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, computer program and medium have similar and/or identical preferred embodiments as the claimed device and as defined in the dependent claims.

This invention describes a non-invasive, real time, user-friendly and reliable dehydration diagnostic approach for identifying older/younger people at risk at the early stages of dehydration, e.g. to enable the timely intervention of the caregiver with proper treatment.

The invention is based on an optical assessment of the dryness of a tissue portion by evaluating the reflectivity of the tissue portion at its surface. A well-hydrated tissue portion is wet and shiny and reflects more light than a dehydrated tissue portion. To exploit this, it is proposed to emit light into the tissue portion and to determine the amount of reflected light. The intensity of directly reflected light (in relation to the intensity of the emitted light) is proportional to the reflectivity of the tissue portion. This again is proportional to the wetness of the tissue portion, in other words the tissue hydration.

Not all light is reflected at the surface of the tissue portion. Some light also enters the tissue portion and is backscattered. It is desired to obtain a measure for the amount of light that is reflected at the surface of the tissue portion and not backscattered. Light that is directly reflected at the tissue surface will not change its polarization. In contrast thereto, light that has entered the tissue and is backscattered will be depolarized.

Thus, for obtaining a reliable measurement, it is proposed to use light of varying polarization (non-polarized light) that is emitted by a light source. Prior to an interaction of the light with the tissue portion, i.e. prior to the light reaching the tissue portion, at least part of the emitted light is polarized. For this, polarization means are included in the device according to the present invention. Consequently, light of known polarization is emitted into (i.e. illuminated onto) the tissue portion. After being polarized, the emitted light interacts with the tissue portion. In particular, at least some of the light is reflected at the surface tissue portion and retains its polarization. Another part will be backscattered from within the tissue and thereby be depolarized. The light having retained its polarization is to be detected by the first light detector. The directly reflected portion of the light is determined by means of a first light detector for detecting polarized light.

This first light detector may include polarization means or a polarization filter. It may, however, also be possible that polarization means are included that are separate from the first light detector. The first light detector is configured to detect light that is polarized in the same way as the at least part of the emitted light after being polarized by the polarization means.

In other words, the portion of light that is backscattered after the interaction (reflection) at the tissue portion and thus depolarized is not detected or blocked and will not reach the first light detector. The amount of directly reflected light, e.g. at 660 nm and at 940 nm, is proportional to the shininess/wetness of the tissue portion. This is directly related to the (de)hydration status of a living being.

The emitted light may preferably have a wavelength of 660 nm or 940 nm (first wavelength), but may also be of other wavelengths. The light may particularly be emitted by one or more LEDs. The wavelength is restricted to the first wavelength (polarized light of the first wavelength is detected) to allow deriving a vital sign parameter and/or to provide defined characteristics.

Often, e.g. when the measurement is performed on a tongue with mouth closed, the influence of ambient light is not very significant. It may also be possible to illuminate the tissue at a certain frequency (e.g. 100-300 Hz) and filter the detected light accordingly for robustness against ambient light influences.

From the determined reflectivity as obtained by measuring the intensity of the reflected polarized light, a measure for the tissue hydration is derived. This tissue hydration parameter can then again be used for determining an index (body hydration index) being indicative of the hydration state of the living being. This index may indicate the hydration state on an absolute or relative scale. In particular, the index may indicate a derivation from a normal state, i.e., provide information about whether or not the body hydration can be considered to be within normal boundaries or not. Both single measurements as well as a monitoring over a time period are possible.

To obtain a meaningful result, a reference measurement of the tissue hydration may be required against which a current measurement can be compared. The body hydration index may either represent this comparison, i.e. include the respective reference value, or may represent only the current measurement that has to be compared to the reference measurement in a further step.

The processing is carried out in processing means that may particularly be connected to both the first light source and the first light detector to control their functionality. The processing means perform the required processing operations for evaluating the sensor readings, deriving parameters therefrom and determining the desired body hydration index.

Preferably, a tissue portion in an oral cavity of a living being, e.g. a tissue portion in the tongue or cheek, may be evaluated. The present invention is particularly suitable for being applied by human beings. In particular, the body hydration index can be used for determining whether a human is sufficiently hydrated or not. However, also an application to other body parts or to other living beings (animals) is possible.

The device and method of the present invention are easily and comfortably applicable. The device may be embodied in the form of a simple handheld device for giving an early warning of dehydration. Thereby, the dehydration screening technique may become more reliable and easy to use even for an un-trained individual. For instance, a device in the form of an oral stick may be applied by a human for measuring his own hydration state or by a caregiver to measure or monitor the hydration state of a caretaker, e.g. in a hospital or elderly care facility etc. In comparison to previous approaches for determining the hydration state of a living being, the application of the device of the present invention requires less training. Thus, it can be easily used in a primary care setting. This is also advantageous for a use in developing countries where the resources are limited in terms of manpower, education and money.

The device and method of the present invention allow a fast and cost-efficient measurement or monitoring of the hydration state of a human being. An early warning for dehydration amongst different home care patient populations, including babies, children in developed and developing countries, elderly, pregnant women, diabetics, and athletes, mountaineers, and soldiers, but in particular the elderly, is provided. It becomes possible to obtain a dehydration assessment in an ergonomic way to allow easy and fast application in comparison to previous approaches that require exchanging parts such as test stripes or that require collecting bio-samples such as saliva or urine or approaches that even rely on invasive techniques.

The device as described herein allows overcoming the shortcomings and problems of previous approaches and may provide a reliable, easy-to-use measurement without requiring an extensive, costly and possibly uncomfortable measurement procedure.

In a preferred embodiment the device further comprises a second light detector for detecting the light of the first wavelength after an interaction of said light of the first wavelength with the tissue portion; wherein the processing means are configured to further derive a tissue color parameter and/or at least one vital sign parameter, in particular a heart rate and/or a breathing rate, from the detected light and to determine the body hydration index further based on said tissue color parameter and/or based on said vital sign parameter. In addition to the light directly reflected at the surface of the tissue portion (i.e. the polarized light detected by the first light detector) also the light that has interacted with the tissue portion differently (e.g. backscattered) is detected. The second light detector captures depolarized light. In particular, the second light detector thus captures both backscattered light and light being reflected at the surface. The second light detector may also be configured to capture transmitted light, i.e. be positioned so that the tissue portion is between the first light source and the second light detector. Based on the detected light of the second light detector, the processing means may perform a photoplethysmography (PPG) processing. Temporal variations in blood volume in the tissue portion lead to variations in light absorptions by the skin. These are observed and a PPG signal (also called, among other, a pleth wave) is obtained. Based thereupon, a vital sign such as the heart rate or the breathing rate can be derived. For this, the periodic fluctuation (AC component of the PPG signal) may be evaluated. An insufficiently hydrated person may have a higher heart rate and/or a higher breathing rate.

Furthermore, it is also possible to derive a tissue color parameter by means of the second light detector and based upon the PPG signal. This parameter may also be referred to as tissue darkness parameter. For this, the level of the PPG signal (DC component of the PPG signal) may be evaluated. The darker the color of the tissue, the lesser it may be hydrated.

Thus, both the derived vital sign and/or tissue color parameter carry further information on the hydration state of the living being. The processing means are configured to also include these parameters when determining the body hydration parameter. This allows further increasing the validity of the determined body hydration index and increasing its significance with respect to the hydration state of the living being.

In a preferred embodiment, the device further comprises a second light source for emitting light of a second wavelength into the tissue portion of the living being; a second light detector for detecting light of the first wavelength and light of the second wavelength after an interaction of said light of the first wavelength and said light of the second wavelength with the tissue portion; wherein the processing means are configured to further derive a tissue color parameter and/or at least one vital sign parameter, in particular a heart rate, a breathing rate and/or a blood oxygen saturation, from the detected light and to determine the body hydration index further based on said tissue color parameter and/or based on said at least one vital sign parameter. If additionally a second light source is provided it becomes possible to further obtain a reading for the blood oxygen saturation (SpO2). Preferably, red and infrared light are emitted by the two light sources. The second light source emits light of the respective other wavelength in comparison to the light emitted by the first light source. The second light detector captures light of both wavelengths and of all polarizations. Thus, reflected, backscattered and/or transmitted light (depending on the arrangement) can be detected.

The tissue color parameter and vital sign that may be determined as outlined above but with a higher accuracy due to a redundancy of the two wavelengths. Additionally, PPG processing of light of two wavelengths can be used to derive a reading for the blood oxygen saturation. Thereby, the absorption characteristics of blood for light of different wavelengths (which is different for different levels of blood oxygenation) are exploited. This reading of the blood oxygen saturation may be used to distinguish a state in which the living being has abnormal vital sign values (e.g. an elevated heart and breathing rate) due to dehydration from other reasons. By including the second light source and the second light detector, it is thus possible to further increase the validity of the determined body hydration index with respect to the hydration state of the living being.

In another embodiment the device further comprises a contact impedance sensor for determining an impedance parameter of the tissue portion; wherein the processing means are configured to derive the tissue hydration parameter further based on said impedance parameter. The contact impedance sensor will usually include at least two electrodes. An electric current can be used to assess the bio impedance of the tissue portion. For instance, a low level sinusoidal current at a single frequency or multiple frequencies (Hz-MHz) can be employed for measurement. The total impedance will rise in the case of a dry tissue portion. This may be an indication of dehydration. The processing means can include the reading of the impedance sensor when determining the body hydration parameter. Additionally including the outlined contact impedance sensor may allow further increasing the reliability and validity of the determined index.

In yet another embodiment the device further comprises a temperature sensor for determining a temperature parameter being indicative of a body temperature of the living being; wherein the processing means are configured to determine the body hydration index further based on said temperature parameter. Such a temperature sensor may be incorporated by a simple thermistor. The temperature sensor allows a temperature of the tissue portion to be measured. For this, the temperature sensor will usually need to be in contact with the tissue portion. The temperature of the tissue portion is an indication of the body temperature of the living being. Dehydration will usually result in an elevated core body temperature. Additionally, an elevated body temperature increases body water excretion through skin and lungs. Thus, the temperature may be used as an additional input parameter when determining the body hydration index to further increase the validity and reliability of the determined body hydration index.

In a further embodiment the device further comprises a respiration sensor for determining a respiration signal; wherein the processing means are configured to further derive a respiration parameter from the determined respiration signal, in particular a breathing rate, and to determine the body hydration index further based on said respiration parameter. In an embodiment that is to be used in the mouth of a living being (the tissue portion particularly being a part of the tongue of the living being), a respiration parameter may be determined by analyzing a respiration signal.

In particular, a respiration signal corresponding to an air pressure signal may be captured and a breathing rate corresponding to the respiration parameter may be determined by analyzing the development of the pressure in the mouth. Usually, the development of the pressure over time will have a periodic characteristic. Therefrom, it is possible to derive the breathing rate. As outlined above, an increased breathing rate may indicate dehydration. The respiration sensor can provide a reading of the breathing rate or of another respiration parameter that may be used in addition or alternatively to a breathing rate obtained by means of PPG. Again, the validity of the determined body hydration index can be increased since further information is considered.

In yet another embodiment of the device as outlined above, the processing means are configured to further determine a pulmonary parameter being indicative of a pulmonary problem of the living being based on the at least one vital sign parameter and the temperature parameter. The application of the device of the present invention can be broadened from dehydration only to fluid status in general, covering both dehydration and fluid retention. If a reading for the blood oxygenation is available, a low value in combination with a high breathing rate can indicate pulmonary fluid retention (e.g. an edema). Also it may be possible to obtain information about a potential pneumonia. This may be determined by the processing means in the form of a pulmonary parameter. Such a parameter may be a binary parameter indicating a problem or also a multidimensional parameter that indicates a type of problem and its severity. Consequently, this embodiment allows providing a monitoring function with respect to the wellbeing of a living being.

In yet another embodiment the device further comprises a beam splitter arranged between the first light source and the tissue portion for guiding the emitted light into the tissue portion and for guiding the light reflected at the tissue portion to the first light detector. The beam splitter might be attached to the first and/or second light sources. The beam splitter guides the emitted light to the tissue portion and from there to the first and/or second detectors. The coupling with the tissue portion is then still glass- or plastic-based such that an adequate in-coupling of the light into the tissue portion is assured. The inclusion of a beam splitter may particularly result in a more accurate reading since fewer disturbances from ambient light will be observed.

Preferably, the beam splitter is polarization-sensitive; and/or the polarization means are integrated with the beam splitter. The beam splitter thus additionally provides the polarization filtering functionality. Thereby, it can be assured that the even if a regular light detector is used as the second light detector, only polarized light of the correct polarization is detected. On the one hand, the beam splitter may integrate the first polarization means, i.e. polarize at least part of the light emitted by the first light source (into the beam splitter). On the other hand, the beam splitter may also polarize the reflected light (i.e. apply a polarization-sensitive filter) after the interaction with the tissue portion and prior to being captured by the first light detector. Thereby, it can be assured that the first light detector only detects polarized light of the first wavelength.

Furthermore, in an embodiment, the first light detector includes second polarization means for polarizing incident light. Alternatively, it is also possible that the first light detector also includes polarization means for polarizing the incident light. If the light is not polarized after the interaction and prior to being detected by the first light detector by means of a beam splitter or other optical components, it may also be possible that the first light detector includes polarization means comparable. The second polarization means polarize the light with the same polarization as the first polarization means. Advantageously, this may also allow using a standard light detector as the first light detector.

In yet another embodiment the processing means are configured to determine the body hydration index based on comparing a parameter with a predetermined reference parameter. Preferably, one or more of the derived sensor parameters are compared to one or more predetermined reference parameters to assess whether or not the parameter is within normal range and/or to which extend the parameter derives from this normal state. Such a predetermined reference parameter may be determined in a clinical assessment in which a reference parameter set is established at a time when it is assured that the living being is sufficiently hydrated. The predetermined reference parameter may also be obtained from a database comprising parameters of other living beings, in particular other living beings that are comparable with respect to parameters such as age, gender, physiology, etc. Then, a statistical definition of a normal range may be obtained.

In yet another embodiment the device further comprises interface means for providing feedback information to a user, the feedback information in particular including the body hydration index. The user may particularly refer to the living being himself (in the case of a human being), to his family or to a physician/caregiver. The interface means allow providing feedback information. This feedback information may particularly include the body hydration parameter. However, there may also be provided the readings of one or more sensors or preprocessed information based on these readings. Furthermore, it is also possible that recommendations of possible courses of action are provided as feedback. The interface means may be incorporated in the form of a display, or any other visual, acoustical or haptic feedback means.

In a preferred embodiment, the device comprises a housing configured to be in contact with a tongue of the living being comprising the tissue portion. Such housing may particularly have the form of stick or the like to be hold in a hand of a human being for being applied orally. The tissue portion of interest is included in the tongue of the living being. The properties of the tongue and the mouth of a human being are advantageous for applying the above-outlined sensor and processing principles such that it becomes possible to obtain a body hydration index that has a high validity with respect to the hydration state. Thus, a mobile, quick and reliable assessment of the hydration state of the living being becomes possible.

BRIEF DESCRIPTION OF THE DRAWINGS

These and other aspects of the invention will be apparent from and elucidated with reference to the embodiment(s) described hereinafter. In the following drawings FIG. 1 schematically illustrates the function of a preferred embodiment of a device according to the present invention;

FIG. 10 shows a top view and a bottom view of the device illustrated in FIG. 9; and FIG. 11 schematically illustrates a method according to the present invention.

DETAILED DESCRIPTION OF THE INVENTION

Figure 1:
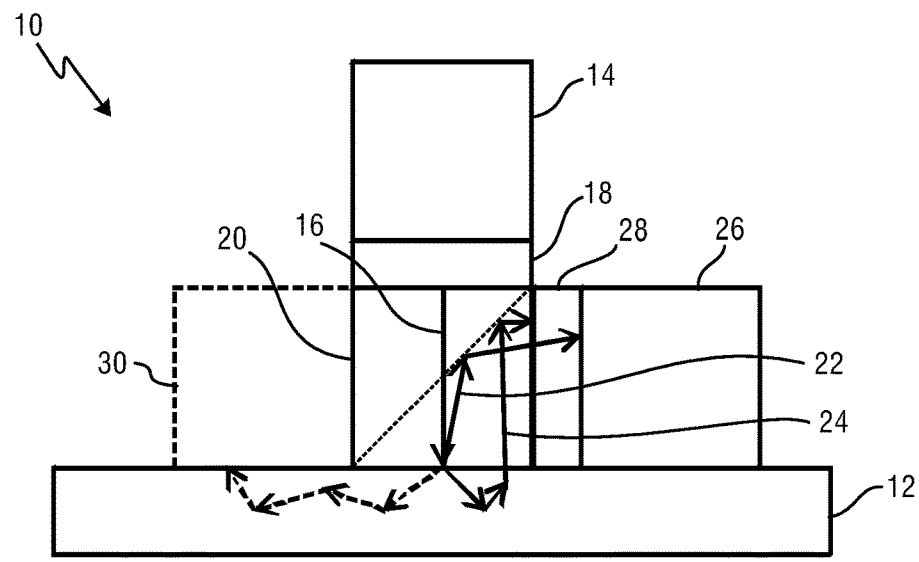

In FIG. 1 a device 10 for measuring a hydration state of a living being according to an embodiment of the present invention is illustrated. In order to derive a body hydration index being indicative of the hydration state of the living being, the reflectivity of a tissue portion 12 is assessed. A first light source 14, preferably incorporated by a LED, emits light of a first wavelength into the tissue portion 12. Prior to entering the tissue portion 12, at least part of the light is polarized by means of polarizing means 18. In the embodiment of FIG. 1 the emitted light passes through a beam splitter 20. Thereafter, the emitted light interacts with the tissue portion 12. The interaction particular corresponds to a reflection of a portion of the light at the surface of the tissue portion 12. Another portion of the light may be backscattered. The arrows in FIG. 1 illustrate possible paths of the emitted light 16, the light portion 22 that is directly reflected at the surface and the light portion 24 that is backscattered.

According to the present invention the portion 22 of the light that is backscattered at the surface is used as an indicator of the surface reflectivity which is directly related to the moisture of the surface, i.e. to the tissue hydration. To obtain a measure for this light portion and to discriminate it from the backscattered light 24, it is exploited that the surface reflection does not affect the polarization of the light whereas the backscattering depolarizes the light.

Consequently, it is possible to detect only the reflected portion 22 of the light by means of a first detector 26 for detecting polarized light. This detector 26 may particularly be incorporated in the form of a photodiode. In the illustrated embodiment, there are included second polarization means 28 for polarizing the light prior to being detected. However, it may also be possible to make use of a polarization sensitive photodetector. As used herein, polarizing corresponds to polarization-sensitive filtering.

Based on the detected polarized light a parameter is derived that is indicative of the hydration of the tissue portion 12. Usually, it will be sufficient to compare the intensity of the captured reflected polarized light with a predetermined reference value in the form of a look-up operation. Also, it may be possible to apply a linear or non-linear transformation function. Such a function or such a lookup table may, e.g., be established experimentally in a reference measurement campaign.

The body hydration index may be given on a relative or absolute scale. For instance, a percentage value may be determined that allows a physician to immediately obtain information on whether or not a person is sufficiently hydrated. Also, a body hydration index in the form of a simple color code (e.g. red and green) may be determined to provide feedback to the user of the device about whether it is necessary to drink more or not.

The derived tissue hydration parameter is then used as a basis for determining a body hydration parameter. This body hydration parameter is indicative of a hydration state of a living being. In particular, it is interesting to obtain information about whether or not and/or to which degree a living being is dehydrated. This may be of relevance in elderly care application but also for children or for persons that suffer from a plurality of health conditions.

In preferred embodiments the device according to the present invention combines several physiological indices of dehydration in a single tool, to provide a quick, automatic, and reliable indication of human hydration status. For this, preferably a tissue portion of a human tongue is analyzed (the invention is, however, not limited to tissue portions in a tongue but may also be applied for other tissue portions, e.g. in the cheek of a human etc.). Dry tongue is a common symptom that physicians visually inspect for in order to identify early signs of dehydration. However, dry tongue alone may sometimes not be sufficient to predict dehydration as the saliva flow rate from the parotid gland may be reduced due to comorbidity, medications or even an open mouth during sleep. Thus further sensors may be added.

As illustrated in FIG. 1 it is optionally (indicated by the dashed line) possible to also detect backscattered light by means of a second light detector 30. This may allow obtaining a PPG signal. Based on this signal, it is possible to derive a vital sign of the living being. Such a vital sign (e.g. the heart rate or the respiratory rate) can be used as an additional input for deriving the body hydration parameter.

Thus, it may also be possible to determine the tissue hydration parameter by determining the amount of reflected light (with maintained polarization, detected by means of the first light detector) divided by the amount of backscattered light (depolarized, detected by the second light detector). In the backscattered light, also the pulse rate, which increases in dehydration, can be derived by photoplethysmography (PPG). The reflected light indicates the shininess of the tissue but in the backscattered light also the PPG signal is captured. When a second light source is added, the reflectivity of the tissue can be determined more accurately and a shift in color can be seen by, e.g., determining the reflectivity at the first wavelength divided by the reflectivity at the second wavelength. Furthermore, the backscattered PPG signals at both wavelengths can be used to derive a SpO2 value (albeit that SpO2 has no clear relation to dehydration).

Figure 2:
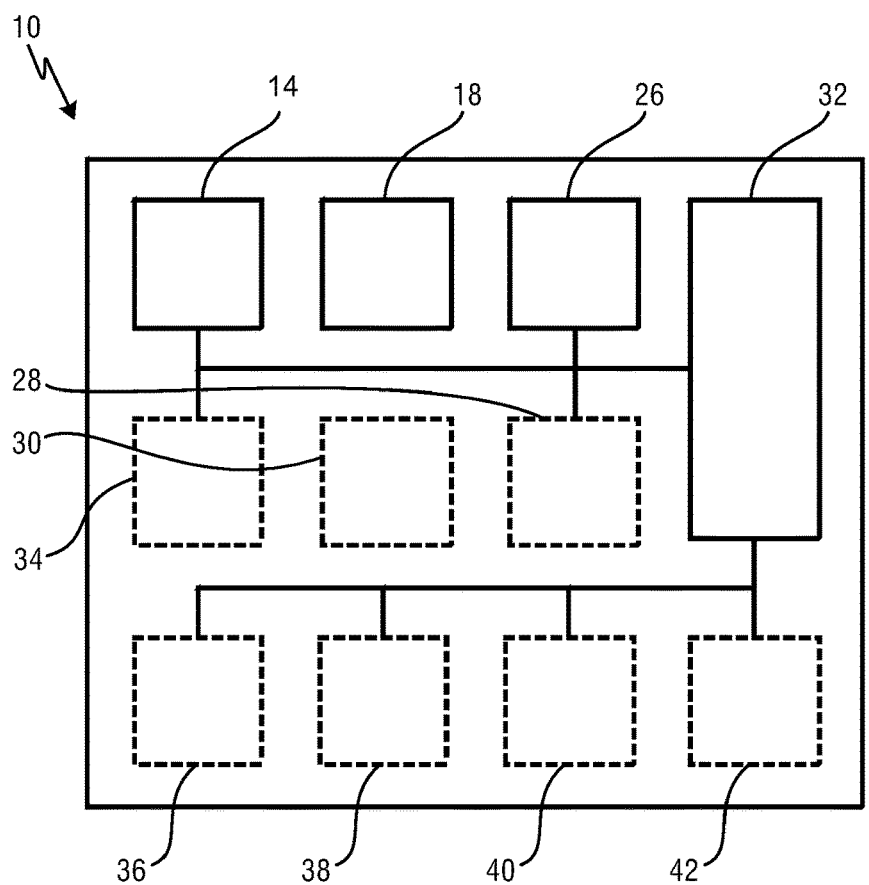
FIG. 2 schematically illustrates the different mandatory and optional components of a device according to the present invention.

FIG. 2 schematically illustrates the different components that may be included in embodiments of a device 10 according to the present invention. The dashed lines indicate optional components. Solid lines indicate that the components are mandatory.

The processing means 32 may particularly be represented by a microprocessor (IC, ASIC, FPGA, etc.). The processing means 32 are connected to the further components by means of a wired or wireless connection. Usually, a plurality of direct connections to the different components may be included. However, it is also possible that a sort of bus system is used. The processing means 32 process the different parameter obtained by different sensors to derive therefrom at least the body hydration index. The processing of the processing means will be further detailed with reference to FIGS. 6 and 7.

In addition to the above-explained first light source 14, polarizing means 18 and first light detector 26 there may be comprised a second light source 34, second polarization means 28 as well as a second light detector 30. It has to be noted that the illustration in FIG. 2 is only for illustration. The positions of the components in FIG. 2 are not indicative of how the components interact.

In particular, the second light detector 30 will usually capture depolarized light of the first wavelength that has been emitted by the first light source 14. The second light detector 30 will usually detect light of all polarizations of the first wavelength (emitted by the first light source 30) and light of all polarizations of the second wavelength emitted by the second light source 34. For this, the first and second light sources may preferably be operated in time multiplexing mode and/or synchronized with the second light detector 30. The first and second light detectors will usually include a (polarization sensitive) photodiode for detecting light of a certain bandwidth. The first and second light sources will usually include at least one LED. In particular, the first light source 14 may include a LED for emitting red light (wavelength 660 nm) and the second light source 34 may include a LED for emitting infrared light (wavelength 960 nm) or vice versa. Usually, the light sources and the light detectors will be in direct contact (directly coupled) with the tissue portion. It may, however, also be possible that an optical component is arranged in between (e.g. a beam splitter). The parameters that can be obtained from the evaluation of the signals captured with the first and second detectors will be further explained with reference to FIGS. 3 and 4.

It is possible that the second polarization means 28 are integrated with the first light detector 26 to assure the detection of polarized light. Also, it is possible that the second polarization means 28 are integrated in a polarizing beam splitter. Both the first and the second polarization means may include a linear polarizer (e.g. absorptive or beam-splitting polarizers) and/or a circular polarizer.

Furthermore, the device 10 may include a contact impedance sensor 36 for determining an impedance parameter of the tissue portion. In addition to deriving the tissue hydration parameter from the detected reflected polarized light, another measurement of the same parameter may be obtained by means of a bio impedance analysis. For such a bio impedance analysis a contact impedance sensor 36 may be used. For instance, two or four miniaturized (size ~mm2) electrodes may be brought in contact with the tissue portion. A low level sinusoidal (or any other signal) current at a single frequency or multiple frequencies (Hz-MHz) can be employed for measurement. The total impedance will rise in the case of dry tissue. This measurement may be combined with the above-outlined reflectivity analysis to further increase reliability and validity when determining the body hydration index.

Still further, a temperature sensor 38 may be included for providing a reading of a temperature of the tissue portion. This temperature may be considered to be indicative of a core body temperature of the living being. The temperature sensor 38 may include a simple thermistor (epoxy, composites etc.) to be brought in contact with the tissue portion. Dehydration usually results in an elevated core body temperature. Additionally, an elevated body temperature increases body water excretion through skin and lungs.

Some embodiments of a device according to the present invention may also include a respiration sensor 40 for obtaining a respiration signal. This is particularly relevant when the device of the present invention is applied in the mouth of a living being since a breathing rate (corresponding to a respiration signal) can carry further insights about the dehydration state. For instance a breathing rate can be derived from the air pressure in the mouth of a living being. This is further illustrated with respect to FIG. 5.

In some embodiments interface means 42 may be comprised in the device 10 to provide feedback information to a user. The feedback information may particularly be provided to a human being using the device 10. Then, the human being may himself obtain feedback on his hydration state. Also, a physician or caregiver may obtain the feedback information about his patient. The interface means may include a display for visualizing parameters and the determined body hydration index. It may, however, also be possible that the interface means include means for wired or wireless communication. Then, parameters and/or the body hydration index may be communicated to a database or forwarded to another recipient (e.g. in remote care or surveillance facilities).

Figure 3:
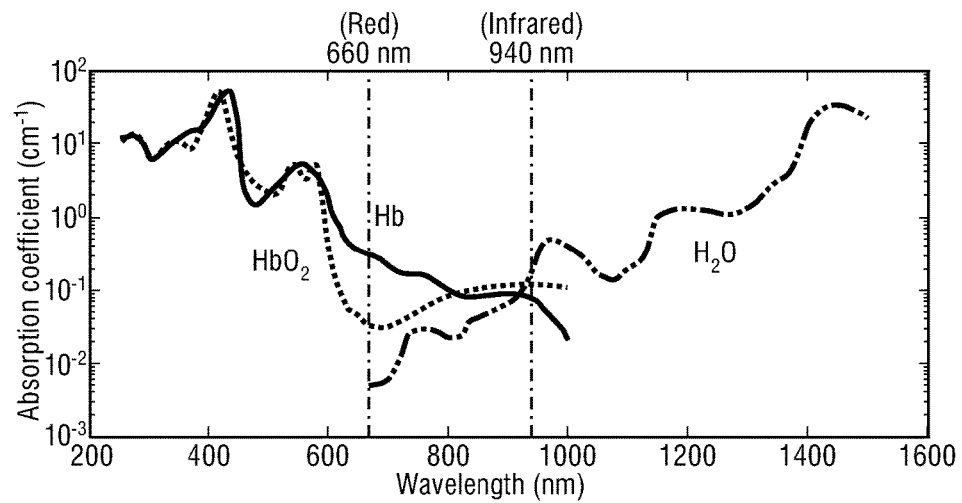
FIG. 3 shows the variation of the absorption (extinction) coefficients of oxyhemoglobin, hemoglobin and water in dependence of the wavelength.

FIG. 3 illustrates the absorption coefficients of oxyhemoglobin, hemoglobin and water as a function of the wavelength. In embodiments of the present invention that include two light detectors it is possible to exploit these characteristics. For instance, a measure for the tissue hydration may be obtained by means of two-wavelength DC spectroscopy using LEDs as present in a pulse oximeter (e.g. 660 nm and 940 nm). To improve the robustness of this method, the LEDs can switch from >125 Hz (<8 ms) illumination (for photoplethysmography and pulse oximetry) to longer illumination times of multiple seconds to measure the average reflection at both wavelengths over multiple heartbeats. Since the tongue of a dehydrated person is more purplish than the tongue of a well-hydrated person, the tongue will reflect less red light (e.g. 660 nm) and approximately the same amount of near-infrared light (e.g. 940 nm), since the difference in absorption between Hb and HbO2 is much smaller in the near-infrared region compared to in the red region (see FIG. 3). Hence, a measure of a tissue darkness/purpleness can be expressed by the ratios R=DC660 nm/DC940 nm or R=DC660 nm/(DC660 nm+DC940 nm), which both decrease when the tissue is more dark/purplish. Also an equation, e.g. in the form of a*R+b, can be used, in which the constants a and b may be empirically determined in calibration experiments and R is one of the ratios.

Furthermore, a tissue hydration parameter may also be obtained if another near-infrared LED is available (e.g. included in the second light source) that emits light in the region where absorption by hemoglobin is very small (or zero) and that of water is quite strong. Proper wavelengths may be the two peaks in as illustrated in FIG. 3 at ~1000 nm and ~1200 nm. When a wavelength below 1250 nm is chosen, a standard photodetector for pulse oximetry might still be used for the detection. However, when longer wavelengths are used, a dedicated photodetector is required. When the tissue portion is wet or less dry, it contains more water. Therefore, more near-infrared light will be absorbed. Hence, a measure of tissue dryness may also be expressed by, as, e.g., DCnearinfrared, R=DCnearinfrared/DC660 nm, or R=DCnearinfrared/(DC660nm+DCnearinfrared), which all decrease when the tissue portion becomes more dry. Alternatively and comparable to the above-explained, an equation in a form such as a*R+b, in which a and b are constants to be empirically determined in calibration experiments, and R is one of the ratios, can be used.

Figure 4:
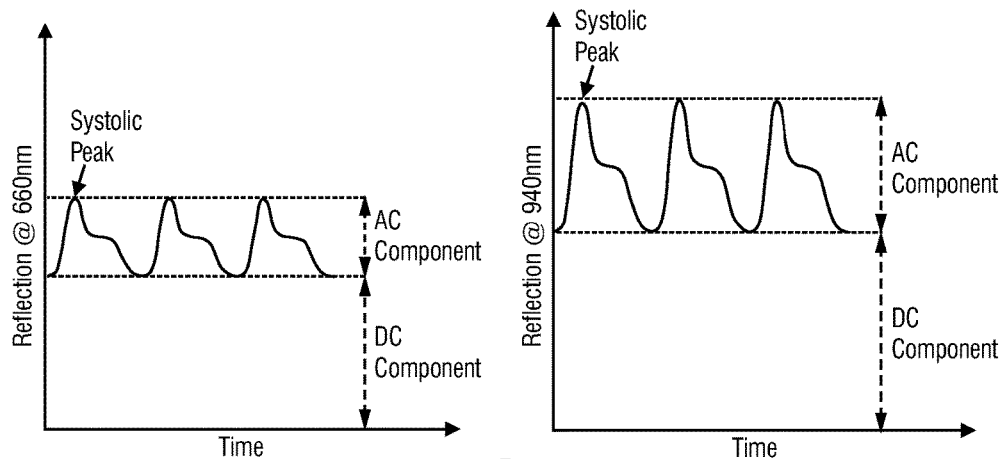
FIG. 4 illustrates the extraction of different parameters being indicative of vital signs of a living being from a PPG signal.

In FIG. 4 it is illustrated how a PPG signal may be processed to derive therefrom a vital sign and/or a tissue color parameter. On the left hand side, FIG. 4 illustrates a PPG signal at a wavelength of 660 nm. On the right hand side, a corresponding signal for a wavelength of 940 nm is illustrated. It is to be understood that these wavelengths represent examples and do not limit the present invention. In embodiments of the present invention usually the first light source will emit light of the first wavelength and the second light source will emit light of the second wavelength. After an interaction with the tissue portion, the light of both wavelengths is detected by the second light detector. Depending on whether one or two light sources are available, different possible information processing approaches can be applied. For obtaining a tissue color parameter, already light of one wavelength is sufficient. Also, some vital sign parameters such as the heart rate and the breathing rate may be determined based on light of one wavelength. For this, PPG processing may be used. The heart rate can be derived from the AC component and the tissue color parameter can be derived from the DC component of the resulting PPG signal, respectively.

Figure 5:
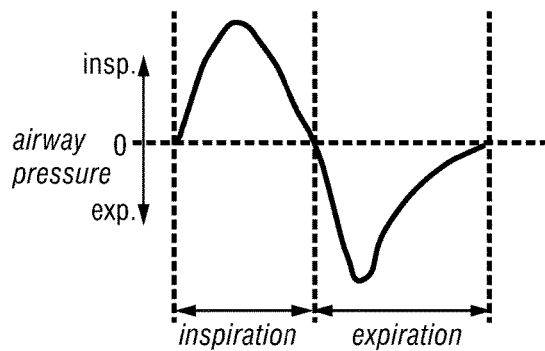
FIG. 5 illustrates the extraction of a breathing pattern from a an air pressure signal.

In FIG. 5 it is illustrated how the air pressure in the mouth of a living being changes during a breath. In case the device of the present invention is applied for a tissue portion in the tongue of a living being and includes a respiration sensor it is thus possible to derive a breathing rate or ventilation rate representing a respiration parameter from the respiration signal of this sensor and include it when determining the body hydration parameter.

Figures 6, 7:
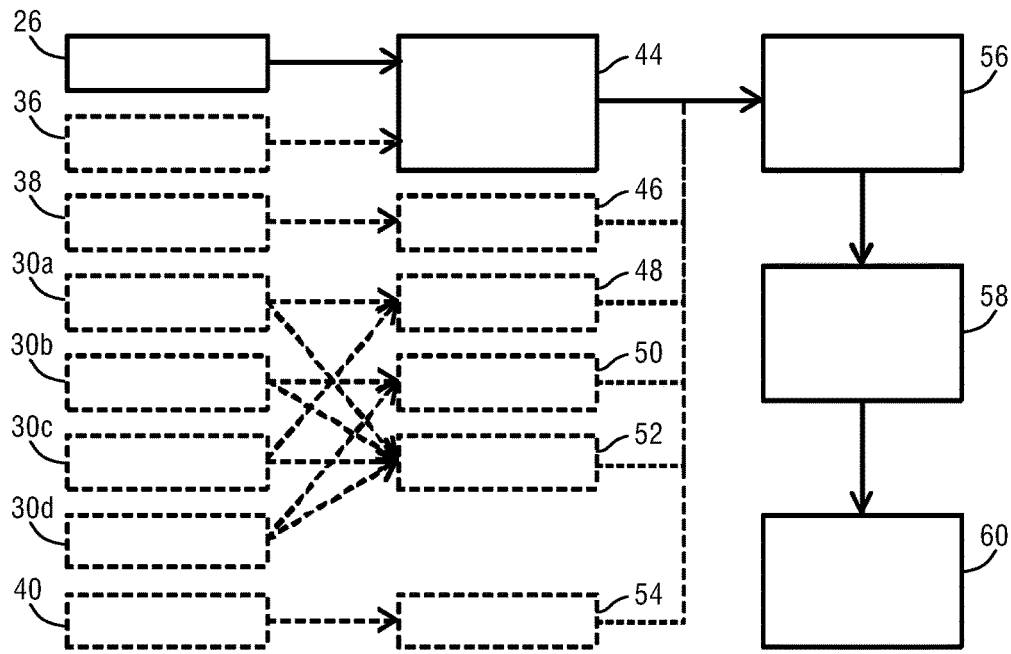
FIG. 6 schematically illustrates the information processing of the present invention.
FIG. 7 gives an example of the determination of a body hydration parameter according to the present invention.

In FIG. 6 an overview of the information processing according to preferred embodiments of the present invention is provided. Depending on the embodiments, the sensors (illustrated in the first column on the left hand side) may include the first light detector 26 that outputs the intensity of the reflected polarized light, a contact impedance sensor 36, a temperature sensor 38 and a respiration sensor 40. Furthermore, a second light detector 30 may provide a reading for the DC level 30a and AC level 30b of the PPG signal derived from the light of the first wavelength and a reading for the DC level 30c and AC level 30d of the PPG signal derived from the light of the second wavelength.

As illustrated in the second column of FIG. 6, the different sensors allow deriving a plurality of different parameters or sensor readings. Based on the signal of the first light detector 26 a tissue hydration parameter 44 being indicative of the hydration or wetness of the tissue portion is derived. If also a contact impedance sensor 36 is available the accuracy of this tissue hydration parameter 44 or the robustness of the measurement can be increased. Thus, the contact impedance sensor 36 may be used for providing redundancy, e.g. in situations with disturbing ambient light etc. Alternatively, it is also possible to combine the readings of the two sensors by averaging with equal, individual or even adapted weights.

The temperature sensor 38 provides a reading that is indicative of the (core) body temperature 46 of the living being. The tissue color parameter 48 can be derived from either the DC level 30a of the light of the first wavelength or from the DC level 30c of the light of the second wavelength. Again, if both readings are available a higher accuracy or redundancy may be obtained. Also the heart rate 50 may be obtained by one or both of the AC levels 30b, 30d of the light of the first and second wavelength. In order to derive a reading for the blood oxygen saturation (SpO2) 52 of the living being, it is required to evaluate both the DC levels 30a, 30c and AC levels 30b, 30d of light of both wavelengths. Furthermore, a respiration parameter 54, in particular a breathing rate, but also parameters like the fluctuation of the breathing rate, the breath intensity etc. can be obtained from the respiration sensor 40. Preferably, the respiratory sensor 40 is embodied by an air pressure sensor. However, it is also possible to obtain a reading for the breathing rate from an evaluation of the PPG signals or from the temperature (by use of the sensors that are already available or by use of separate sensors). This is, however, not illustrated in FIG. 6 for clarity.

The different sensors are combined to derive several tissue-specific (e.g. tissue hydration and color) and whole-body (e.g. heart rate, SpO2, and breathing rate) physiological parameters to assess an individual's hydration status (body hydration index).

In an exemplary embodiment, the parameters are compared to 'normal' reference values and the deviation of 'normal' is determined for each of the parameters in a first processing step 56. Then, the deviations are weighted (based on relative importance of the physiological sign, reliability/quality of the signal measured, weight, age, medical history, etc.) and combined in a second step 58 to obtain an indication of a living being's hydration status, i.e. his body hydration index. Then, feedback may be provided to the living being and/or to his family, caregiver, physician etc. in a third step 60.

In FIG. 7 an example of how parameters can be weighted and combined to assess the degree of dehydration, i.e. to calculate a body hydration index, is illustrated. In the illustrated embodiment, the tissue reflectivity is measured by means of the first light detector for detecting polarized light. Additionally, it is also possible that the tissue impedance is measured and combined with the reading of the first light detector. Furthermore, the tissue color and the heart rate are obtained from a PPG signal obtained by means of a second light detector. Still further, the body temperature is assessed by means of the temperature sensor and the breathing rate is obtained either by means of evaluating the PPG signal or by making use of a pressure sensor.

For each of the available parameters, the deviation with respect to a normal range is scored and at the end, all points are added to arrive at a dehydration score that represents the body hydration index. An example scoring system could be: well-hydrated (0-2 points), mild dehydration (2-6 points), moderate dehydration (6-12 points) and severe dehydration (>12 points).

It is to be noted that while body temperature, heart rate, and breathing rate are all physiological parameters with a known normal range, the values for tissue reflectivity and color depend strongly on the geometry and dimensions of the applied sensors (e.g. spacing between LEDs and photodiode). Therefore, these parameters will usually require a calibration to find 'normal' values and values representing dehydration. Furthermore, the 'normal' values/ranges for all parameters are age-dependent. For instance, the normal heart rate range and breathing rate range for infants are 100-160 beats/min and 30-60 breaths/min, respectively, while for adults these ranges are 60-100 beats/min and 12-16 breaths/min. It is therefore important to incorporate the age of the patient when assessing the degree of dehydration.

In alternative embodiments of the present invention it is also possible to use a linear or nonlinear function that is directly based on the available sensor parameters to determine the body hydration index.

Figure 8:
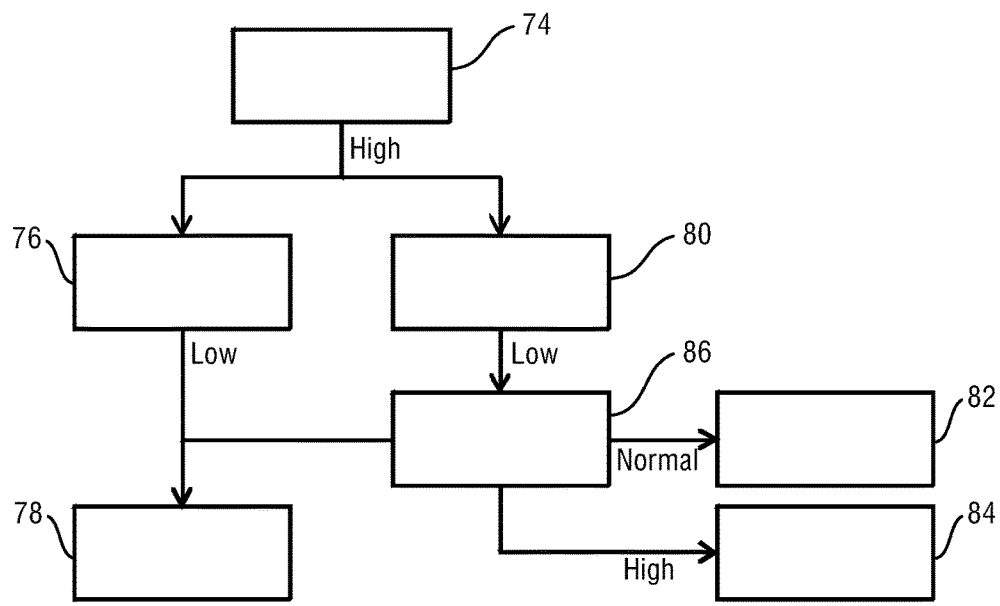
FIG. 8 schematically illustrates how information obtained by a device according to the present invention can be further processed.

In FIG. 8 an example is illustrated for how the addition of SpO2 assessment broadens the application field of a device according to the present invention to the detection of pulmonary problems such as pulmonary edema and pneumonia. Although these pulmonary problems are clinically unrelated to dehydration, they occur in the exact same patient populations that are prone to dehydration; i.e. elderly in developed/developing countries and children mainly in developing countries (dehydration due to diarrhea is the second leading cause of child death worldwide). The elderly in developed countries, besides being prone to dehydration, often also suffer from cardiovascular disease, such as heart failure and hypertension, which cause pulmonary edema. The children in developing countries, on the other hand, are highly susceptible to pneumonia (first leading cause of child death worldwide).

It is illustrated in FIG. 8 how the different parameters can be combined to provide an index reflecting the degree of dehydration (as illustrated in FIG. 7) and give an indication whether pulmonary problems (indicated by low SpO2) are related to pulmonary edema (not associated with fever) or to an infection such as pneumonia (associated with fever).

In a first step 74, the heart rate and the breathing rate are assessed. When both parameters are increased, this can be due to dehydration or due to pulmonary problems. In order to obtain further information on the cause, tissue moisture and tissue color can be assessed (step 76). When the tissue portion has become dry and dark along with the elevated heart rate and breathing rate, this may indicate dehydration 78. The degree of dehydration may be evaluated using a scoring system as described with respect to FIG. 7. When, however, heart rate and breathing rate are elevated and SpO2 is low 80, this may indicate a pulmonary problem (a low SpO2 in combination with a normal heart rate and breathing rate is physiologically not possible). Two common types of pulmonary problems that lead to low SpO2 are pulmonary edema 82 and pulmonary infections 84 such as pneumonia. Since pulmonary infections are associated with a rise in body temperature and pulmonary edema is not, the body temperature 86 can be used to give an indication of the type of a (potential) pulmonary problem.

Clearly, a living being may, e.g., suffer from pulmonary edema (fluid retention) while being dehydrated. This is a common complication in elderly heart failure and hypertension patients.

Figure 9:
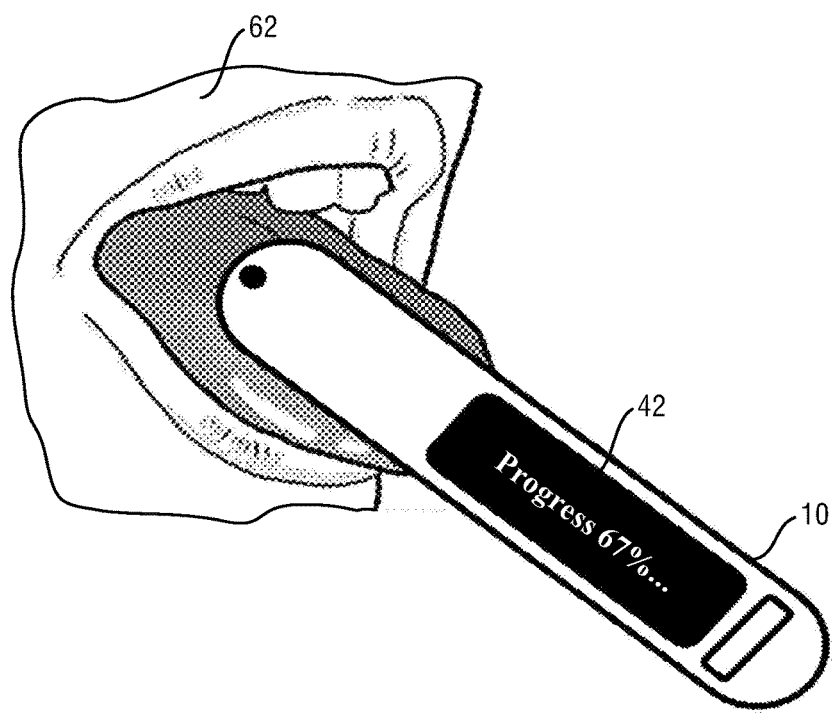
FIG. 9 illustrates the application of an embodiment of a device according to the present invention.

In FIGS. 9 and 10 a preferred embodiment of a device 10 according to the present invention is illustrated. As illustrated, an oral stick for being applied in the mouth of a living being 62 or, more precisely, to a tissue portion of the tongue of the living being 62. The handheld oral stick may comprise a rectangular tip at the end. The tip of the device could be envisioned as a disposable or a semi-disposable to be easily disconnected from the main body of the device. Alternatively the tip of the device may be covered by a transparent (at least for the wavelengths of the first and second light source 14, 34) elastic disposable. Clearly, it is also possible to apply the oral stick to the cheek of the living being. By means of such an oral stick different parameters may be measured simultaneously with a response time of less than a minute. As illustrated in FIG. 9 a progress indication may be provided during the measurement, e.g. by means of a display 42.

In FIG. 10 a top view and a bottom view of the oral stick are further illustrated in greater detail. The device may, e.g., have a length of 10-17 cm at a width of 1-2 cm and a thickness of 0.2-1 cm. The portion of the device to be inserted into the mouth may have a length of 1-2 cm. On the top side 10a, a connector 64, such as a USB connector, may be provided. Further, a display 42 may provide feedback information to a user in the form of the readings of the respective sensors and in the form of a body hydration index (represented by a statement "mildly dehydrated" in the illustrated example). Apart from a connector and/or a display, the interface means may also include a wireless communication module for connecting to a network or to another device. There may be comprised a respiration sensor 40, e.g. in the form of an air pressure sensor or a temperature sensor, based on which a signal can be obtained that is indicative of a respiration parameter such as a breathing rate.

On the bottom side 10b of the device 10 a space 66 for energy storage means or data storage means or for additional communication means (e.g. a wireless interface or wireless network connection) may be provided. Furthermore, the illustrated embodiment of the present invention comprises a first light source 14 that includes two red LEDs and a second light source 34 that includes two infrared LEDs. A photodiode 68 represents the first light detector and the second light detector. In other embodiments two photodiodes may be used. Still further, a contact impedance sensor including two current electrodes 70 and two voltage electrodes 72 (for measuring the voltage across the current path between the current electrodes) is illustrated. The temperature sensor 38 may provide a reading that is indicative of the body temperature of the living being.

In FIG. 11 a method according to an aspect of the present invention is schematically illustrated. The method includes the steps of emitting (step S10) light of a first wavelength, polarizing (step S12) at least part of the emitted light, detecting (step S14) reflected light and deriving (step S16) a tissue hydration parameter and determining (step S18) a body hydration index.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or an does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for measuring a hydration state of a living being, comprising:
   a first light source for emitting light of a first wavelength into a tissue portion of the living being;
   polarization means for polarizing at least part of the emitted light prior to an interaction of the emitted light with the tissue portion;
   a first light detector for detecting polarized light of the first wavelength reflected at the surface of the tissue portion, which has retained its polarization in the reflection;
   a second light detector for detecting non-polarized light of the first wavelength after an interaction of said light of the first wavelength with the tissue portion; and
   processing means configured to:
      compare an intensity of the detected reflected polarized light with a reference intensity,
      derive a tissue hydration parameter based on the comparison,
      derive a tissue color parameter and at least one vital sign parameter, wherein the at least one vital sign parameter includes a heart rate and/or a breathing rate, from the detected non-polarized light, and
      determine a body hydration index based on said tissue hydration parameter, said tissue color parameter and said vital sign parameter.

2. The device as claimed in claim 1, further comprising:
   a second light source for emitting light of a second wavelength into the tissue portion of the living being;
   the second light detector configured to detect non-polarized light of the first wavelength and non-polarized light of the second wavelength after an interaction of said light of the first wavelength and said light of the second wavelength with the tissue portion;
   wherein the processing means is configured to further derive the tissue color parameter and the at least one vital sign parameter, wherein the at least one vital sign parameter includes the heart rate, the breathing rate and/or a blood oxygen saturation, from the detected non-polarized light and to determine the body hydration index further based on said tissue color parameter and based on said at least one vital sign parameter.

3. The device as claimed in claim 2, wherein the processing means is configured to further determine a pulmonary parameter being indicative of a pulmonary problem of the living being based on the at least one vital sign parameter and a temperature parameter,
   wherein the temperature parameter is determined by a temperature sensor and is being indicative of a body temperature of the living being.

4. The device as claimed in claim 1, further comprising:
   a contact impedance sensor for determining an impedance parameter of the tissue portion;
   wherein the processing means is configured to derive the tissue hydration parameter further based on said impedance parameter.

5. The device as claimed in claim 1, further comprising:
   a temperature sensor for determining a temperature parameter being indicative of a body temperature of the living being;
   wherein the processing means is configured to determine the body hydration index further based on said temperature parameter.

6. The device as claimed in claim 1, further comprising:
   a respiration sensor for determining a respiration signal;
   wherein the processing means is configured to further derive a respiration parameter from the determined respiration signal, wherein the respiration parameter includes the breathing rate, and to determine the body hydration index further based on said respiration parameter.

7. The device as claimed in claim 1, further comprising:
   a beam splitter arranged between the first light source and the tissue portion for guiding the emitted light into the tissue portion and for guiding the light reflected at the tissue portion to the first light detector.

8. The device as claimed in claim 7, wherein the beam splitter is polarization-sensitive; and/or
   wherein the polarization means is integrated with the beam splitter.

9. The device as claimed in claim 1, wherein the first light detector includes second polarization means for polarizing incident light.

10. The device as claimed in claim 1, wherein
    the processing means is configured to determine the body hydration index based on comparing a parameter with a predetermined reference parameter.

11. The device as claimed in claim 1, further comprising:
    interface means for providing feedback information to a user, the feedback information including the body hydration index.

12. The device as claimed in claim 1, further comprising:
    a housing forming an oral stick configured to be in contact with a tongue of the living being, the tongue comprising the tissue portion,
    wherein the oral stick includes:
    a disposable tip removably coupled to a body of the oral stick, or
    an elastic disposable cover transparent to light of the first wavelength.

13. The device as claimed in claim 1, wherein the reference intensity includes an intensity of the emitted polarized light.

14. The device as claimed in claim 1, wherein the reference intensity is at the first wavelength.

15. The device as claimed in claim 1, where in the processing means is configured to weight the tissue hydration parameter, the tissue color parameter, and the vital sign parameter relative to each other and determine the body hydration index based on the weighted tissue hydration parameter, tissue color parameter, and vital sign parameter.

16. A method for measuring a hydration state of a living being, comprising the steps of:
    emitting light of a first wavelength into a tissue portion of the living being;
    polarizing at least part of the emitted light prior to an interaction of the emitted light with the tissue portion;
    detecting polarized light of the first wavelength reflected at the surface of the tissue portion, which has retained its polarization in the reflection;
    detecting non-polarized light of the first wavelength after an interaction of said light of the first wavelength with the tissue portion;

comparing an intensity of the detected reflected polarized light with a reference intensity;

deriving a tissue hydration parameter based on the comparison;

deriving a tissue color parameter and at least one vital sign parameter, wherein the at least one vital sign parameter includes a heart rate and/or a breathing rate, from the detected non-polarized light;

and determining a body hydration index based on said tissue hydration parameter, said tissue color parameter and said vital sign parameter.

17. The method as claimed in claim 16, wherein the reference intensity includes an intensity of the emitted polarized light.

18. The method as claimed in claim 16, further comprising weighting the tissue hydration parameter, the tissue color parameter, and the vital sign parameter relative to each other, and determining the body hydration index based on the weighted tissue hydration parameter, tissue color parameter, and vital sign parameter.

19. A non-transitory, machine-readable media storing instructions that, when executed by one or more physical processors, effectuate operations comprising:

emitting light of a first wavelength into a tissue portion of the living being;

polarizing at least part of the emitted light prior to an interaction of the emitted light with the tissue portion;

detecting polarized light of the first wavelength reflected at the surface of the tissue portion, which has retained its polarization in the reflection;

detecting non-polarized light of the first wavelength after an interaction of said light of the first wavelength with the tissue portion;

comparing an intensity of the detected reflected polarized light with a reference intensity;

deriving a tissue hydration parameter based on the comparison;

deriving a tissue color parameter and at least one vital sign parameter, wherein the at least one vital sign parameter includes a heart rate and/or a breathing rate, from the detected non-polarized light; and determining a body hydration index based on said tissue hydration parameter, said tissue color parameter and said vital sign parameter.

20. The non-transitory, machine-readable media storing instructions as claimed in claim 19, wherein the reference intensity includes an intensity of the emitted polarized light.

21. The non-transitory, machine-readable media storing instructions as claimed in claim 19, wherein the tissue hydration parameter, the tissue color parameter, and the vital sign parameter are weighted relative to each other, and the body hydration index is determined based on the weighted tissue hydration parameter, tissue color parameter, and vital sign parameter.

22. A device for measuring a hydration state of a living being, comprising:

a first light source configured to emit light of a first wavelength at into a tissue portion of the living being;

a polarizer configured to polarize at least part of the emitted light prior to an interaction of the emitted light with the tissue portion;

a first light detector configured to detect polarized light of the first wavelength reflected at the surface of the tissue portion, which has retained its polarization in the reflection;

a second light detector for detecting non-polarized light of the first wavelength after an interaction of said light of the first wavelength with the tissue portion; and a processor configured to:

compare an intensity of the detected reflected polarized light with a reference intensity, derive a tissue hydration parameter based on the comparison, derive a tissue color parameter and at least one vital sign parameter, wherein the at least one vital sign parameter includes a heart rate and/or a breathing rate, from the detected non-polarized light, and determine a body hydration index based on said tissue hydration parameter, said tissue color parameter and said vital sign parameter.

\* \* \* \* \*